United States Patent [19]

Pavlanský et al.

[11] Patent Number: 4,878,919

[45] Date of Patent: Nov. 7, 1989

[54] ARTIFICIAL HIP ENDO-LIMB

[75] Inventors: Rudolf Pavlanský; Miroslav Petrtý 1, both of Prague, Czechoslovakia

[73] Assignee: Ceske Vysoke Uceni Technicke, Prague, Czechoslovakia

[21] Appl. No.: 939,643

[22] Filed: Dec. 9, 1986

Related U.S. Application Data

[63] Continuation-in-part of Ser. No. 676,573, Nov. 30, 1984, abandoned.

[30] Foreign Application Priority Data

Nov. 30, 1983 [CS] Czechoslovakia ............... 8930-83

[51] Int. Cl.⁴ .................................................. A61F 2/36
[52] U.S. Cl. ............................................. 623/23; 623/22
[58] Field of Search .................... 623/16, 22, 23, 18, 623/19, 20, 21; 427/2

[56] References Cited

U.S. PATENT DOCUMENTS

| | | | |
|---|---|---|---|
| 3,996,625 | 12/1976 | Noiles | 623/23 X |
| 4,292,695 | 10/1981 | Koeneman | 623/22 X |
| 4,314,381 | 2/1983 | Koeneman | 623/23 X |
| 4,599,085 | 7/1986 | Riess et al. | 623/16 |

FOREIGN PATENT DOCUMENTS 2242867 5/1974 Fed. Rep. of Germany ........ 623/16

Primary Examiner—Richard J. Apley
Assistant Examiner—Alan W. Cannon
Attorney, Agent, or Firm—Klein & Vibber

[57] ABSTRACT

The invention relates to an artificial hip endo-limb comprising a spherical joint supported by a shaft. A porous shell of metal, synthetic material, ceramics and the like is provided on the circumference of the shaft. The porous shell is transversely divided and separated by spacing elements and may be longitudinally divided, and the surface can be provided with grooves.

9 Claims, 3 Drawing Sheets

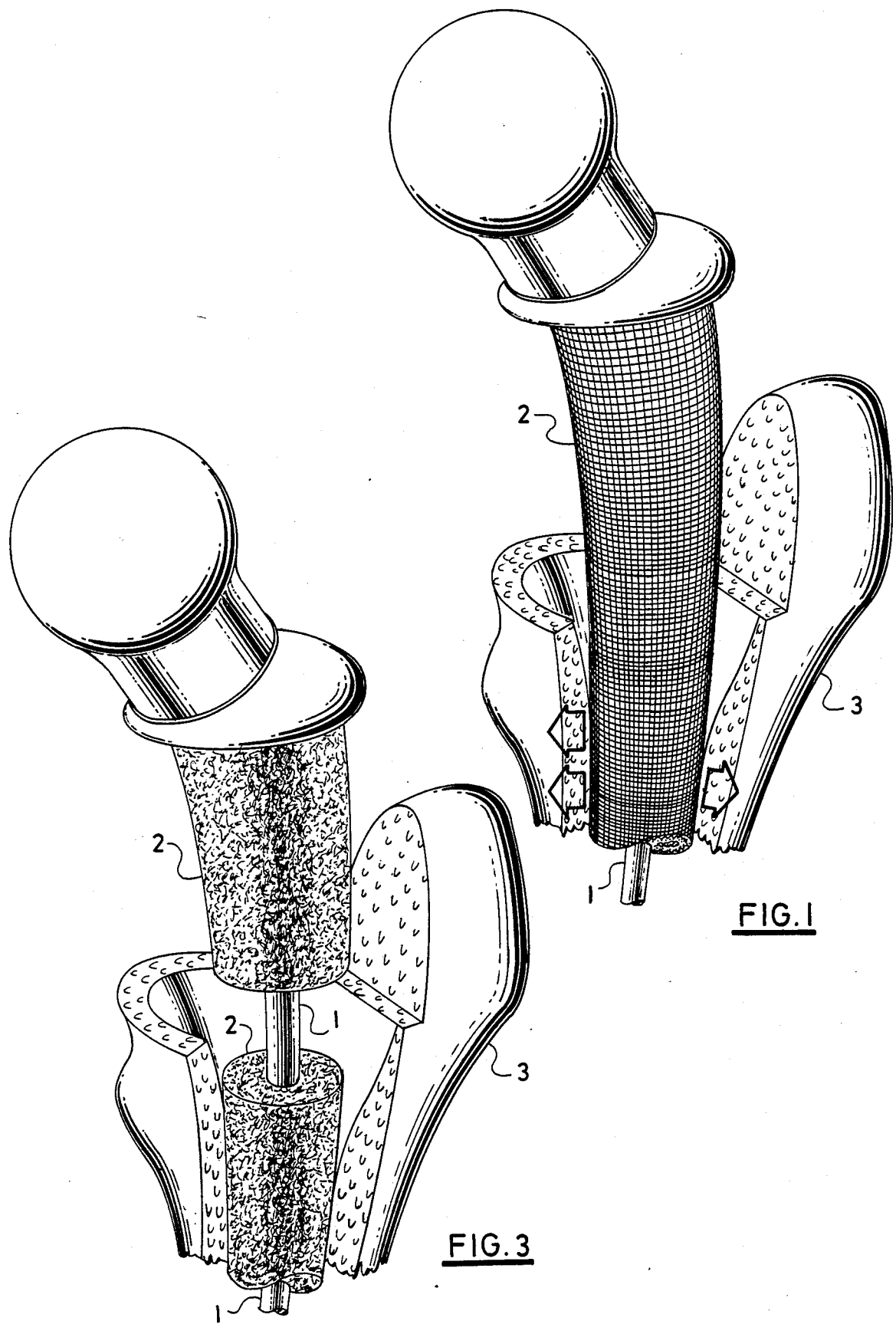

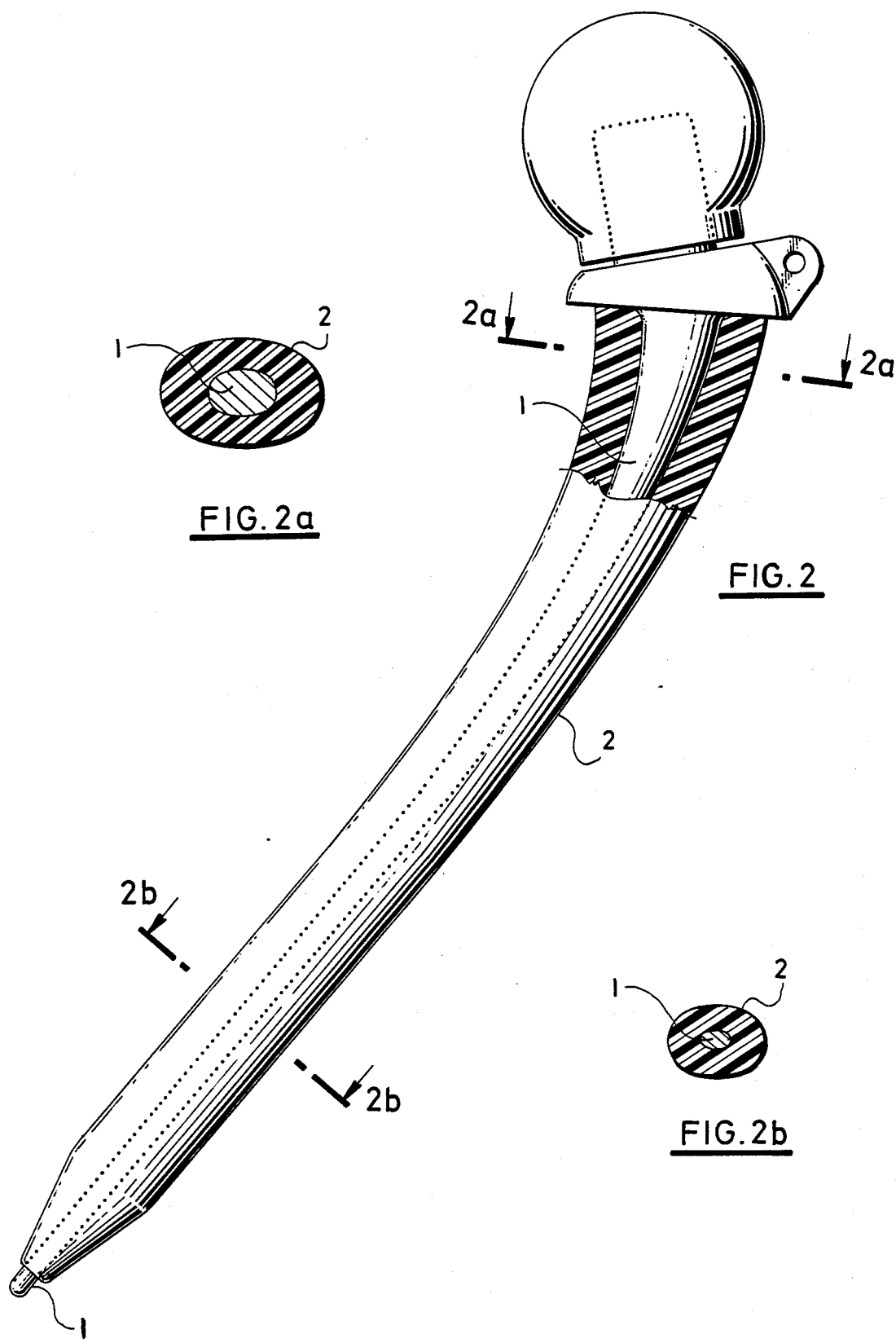

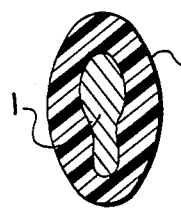
FIG.5
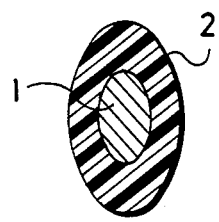
FIG.6
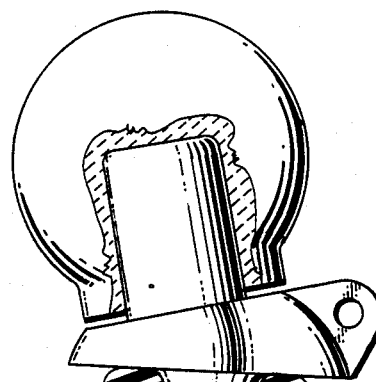
FIG.4
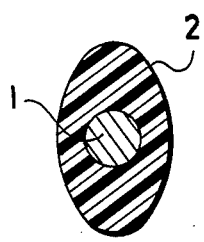
FIG.7
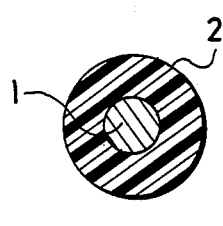
FIG.8
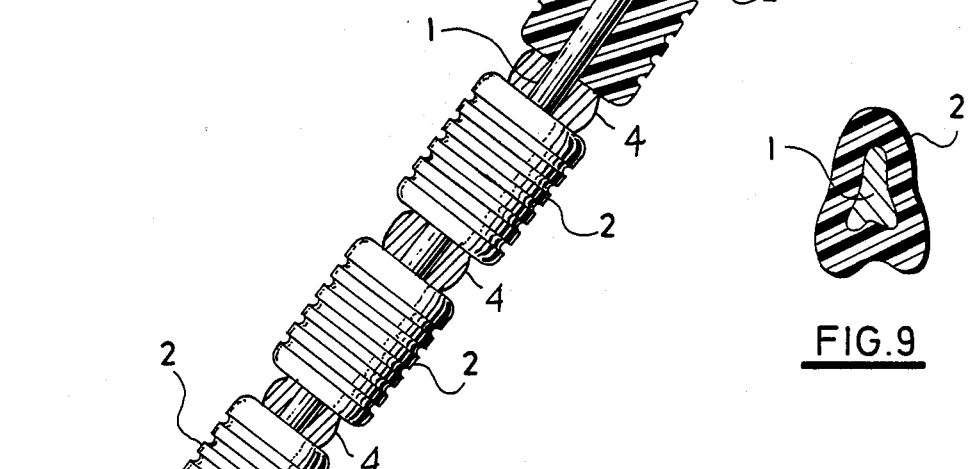
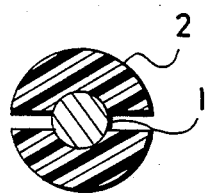
FIG.9
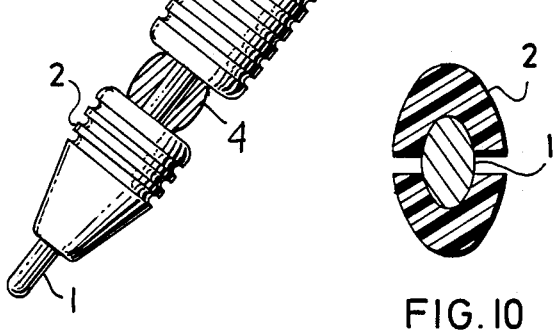
FIG.10  FIG.11

ARTIFICIAL HIP ENDO-LIMB

This application is a continuation-in-part of U.S. application Ser. No. 676,573, filed Nov. 30, 1984, now abandoned.

This invention relates to an artificial hip endo-limb, for use is orthopedic surgery and in cases of motion system trauma.

BACKGROUND OF THE INVENTION

Artificial hip endo-limbs are known in the art, and a variety of polymethylmethacrylate compounds may be used to fasten the artificial limb to the marrow bone of the femur. However, these known bone cements have biological and mechanical drawbacks that frequently result in a loosening of the endo-limb. This in turn results in additional corrective surgical procedures.

Bioceramics are also known, and have been applied to the shafts of artificial hip endo-limbs. Ceramic materials are used for joints or hip pits, because of their high modulus of elasticity, their high degree of hardness, and their ability to transmit high-pressure stresses. However, the material properties of ceramics often result in breakage, even when massive implants are used.

Artificial endo-limbs are described in Heinke (U.S. Pat. No. 4,407,022); Rostoker et al. (U.S. Pat. No. 3,906,550); Koeneman '695 (U.S. Pat. No. 4,292,695); Koeneman '381 (U.S. Pat. No. 4,314,381); Batelle et al. (Dutch Pat. No. 2,242,867) and Noiles et al. (U.S. Pat. No. 3,996,625).

SUMMARY OF THE INVENTION

It is an object of this invention to improve the design of known artificial hip endo-limbs, and particularly their attachment to the narrow bone of the femur.

The artificial hip endo-limb comprises a spherical joint supported by a shaft. According to the invention, a porous shell is provided on the surface of the shaft. The porous shell can be a metal, synthetic material, or ceramic material. The porosity is obtained either by exploiting the properties of the material directly, or by working the material accordingly. For example, a porous metal shell may be achieved by fashioning a sieve-like layer, with chambers in the metal. In a preferred embodiment, a porous ceramic shell is applied to a metallic shaft, and it is advantageous to divide the shell transversely or longitudinally, and to insert spacing elements between individual parts of the shell. In this manner, the attachment of the endo-limb to the marrow channel is further improved.

The artificial limb of the invention represents an improvement over known artificial limbs. It is compatible with living tissue, it does not deteriorate due to chemical and mechanical influences, and the shaft does not loosen. The shaft is free from rupture, and it can be permanently retained by the bone and connecting tissues. The improved endo-limb is biomechanically stable, so that inflammation does not occur and no pathological bone transformations are experienced. After boring or preparation of the bedding by a suitable rasp, the endo-limb can be introduced without complications, and the living tissues are not thermally effected. Undesirable toxic reactions are also eliminated.

BRIEF DESCRIPTION OF THE DRAWINGS

FIG. 1 shows the introduction of the present artificial hip endo-limb into the marrow channel of the tight bone.

FIG. 2 is a longitudinal sectional view with two cross-sectional views.

FIG. 3 is a view of the endo-limb with parts in section showing a transverse division of the shell.

FIG. 4 shows one longitudinal and a number of cross-sectional views of transversely and longitudinally divided porous shells of the shaft of the artificial endo-limb, with spacing elements inserted between shell divisions.

DETAILED DESCRIPTION

The invention is described according to a number of preferred embodiments. It will be understood by those in the art that the embodiments described are merely illustrative, and do not serve to limit the scope of the invention.

The artificial hip endo-limb of the present invention is a composite stiff isoelastic adaptable artificial endo-limb comprising an elastic metallic shaft 1 provided on top with a spherical joint. The shaft 1 is typically constructed of rustless steel, titanium or the like, and is provided on its circumference with a porous shell 2 in the shape of a sieve grid. The grid may have a multiplicity of grid and/or sieve layers, with porous chambers that may be chaotically arranged.

FIG. 1 shows an arrangement where the shell consists of an anticorrosive metal sieve, so that it can be elastically compressed. After introduction into the hollow of tight bone 3, the compressed shell generates a transverse pre-stress pressure, thus mechanically securing the shaft. The porous shell 2 can be divided transversely or longitudinally, and can be in one or more parts.

FIG. 2 shows a porous shell 2 of porous polyamide material. FIGS. 3 and 4 show a porous shell 2 of ceramic material. The shell is transversely divided, and in the embodiment of FIG. 4 is provided with grooves on its external surface. Also as shown in FIG. 4, the cross-section of a metal shaft 1 can be any suitable shape such as circular or oval. The shell can also be longitudinally divided, particularly in cases where no transverse division is provided. If the porous shell 2 is transversely divided, its individual parts can be fixed and stationary on shaft 1, or in the alternative, distancing and fixing elements 4 can be inserted between the parts. The spacing elements 4 can be made of any suitable material such as ceramics, metal, thermoplastic materials, or the like and the insertion of said spacing elements between the basic ceramic elements further improves the ability of scar tissue to grow between the basic ceramic elements which consequently improves the fixation of the stem in the bone cavity as well as allowing it to adapt the elasticity of the stem to the elasticity of the bone.

The present invention permits the use of ceramics, the most suitable material for use in producing a stem combination for an artificial hip endo-limb. However, the invention eliminates the heretofore most serious disadvantage of ceramics: the fragility of the endo-limb stem when subjected to a bending and torsional stress.

According to the invention, the shell may be firmly attached to the metallic shaft; i.e. by welding or via friction, in which case there is an imperceptible overhang. In an alternative embodiment, the shell may be loosly connected to the shaft, in which case the shell is affixed at the lower end, for example by means of an overlay on the end of the shank, and is held in place by pressure.

We claim:

1. An improved artificial hip endo-limb having a spherical joint supported by a metal shaft for insertion in a bone marrow channel, wherein said shaft is surrounded by substantially cylindrical segments of porous ceramic and said segments are transversely separated by substantially cylindrical elastomeric spacing elements which surround the shaft, and wherein said shaft is sufficiently elastic so as to accommodate itself to said bone marrow channel.

2. An artificial hip endo-limb according to claim 1, wherein the outer surface of said porous segments are provided with surrounding peripheral grooves.

3. An artificial hip endo-limb according to claim 1 wherein the porous ceramic transversely separated segments are longitudinally divided.

4. An artificial hip endo-limb according to claim 2 wherein the porous ceramic transversely separated segments are longitudinally divided.

5. An improved artificial hip endo-limb having a spherical joint supported by a metal shaft for insertion in a bone marrow channel, wherein said shaft is surrounded by substantially cylindrical segments of porous ceramic and said segments are transversely separated by substantially cylindrical elastomeric spacing elements which surround the shaft, wherein said separated segments are provided with chaotically arranged porous chambers and with surrounding peripheral grooves on their outer surfaces, wherein said shaft is sufficiently elastic so as to accomodate itself to said bone marrow channel.

6. An improved artificial hip endo-limb having a spherical joint supported by a metal shaft for insertion in a bone marrow channel, wherein said shaft is surrounded by substantially cylindrical segments of porous ceramic and said segments are transversely separated by substantially cylindrical elastomeric spacing elements which surround the shaft, wherein said separated segments are provided with chaotically arranged porous chambers and with surrounding peripheral grooves on their outer surfaces, and wherein each of said segments is longitudinally divided, and wherein said shaft is sufficiently elastic so as to accommodate itself to said bone marrow channel.

7. An artificial hip endo-limb according to claim 1, wherein the surface of the porous shell is provided with peripheral grooves.

8. An artificial hip endo-limb according to claim 1 wherein the porous ceramic transversely separated segments are longitudinally divided.

9. An artificial hip endo-limb according to claim 7 wherein the porous ceramic transversely separated segments are longitudinally divided.

* * * * *